(12) United States Patent
Lesniak et al.

(10) Patent No.: US 6,541,039 B1
(45) Date of Patent: Apr. 1, 2003

(54) NANOSCALE PARTICLES HAVING AN IRON OXIDE-CONTAINING CORE ENVELOPED BY AT LEAST TWO SHELLS

(75) Inventors: Christoph Lesniak, Buchenberg (DE); Thomas Schiestel, Saarbruecken (DE); Helmut Schmidt, Saarbruecken-Guedingen (DE); Andreas Jordan, Berlin (DE)

(73) Assignee: Institut für Neue Materialien gem. GmbH, Saarbrücken (DE)

( * ) Notice: Subject to any disclaimer, the term of this patent is extended or adjusted under 35 U.S.C. 154(b) by 0 days.

(21) Appl. No.: 09/446,438

(22) PCT Filed: Jun. 19, 1998

(86) PCT No.: PCT/EP98/03761
§ 371 (c)(1),
(2), (4) Date: Dec. 20, 1999

(87) PCT Pub. No.: WO98/58673
PCT Pub. Date: Dec. 30, 1998

(30) Foreign Application Priority Data

Jun. 20, 1997 (DE) .......................................... 197 26 282

(51) Int. Cl.$^7$ ................................................. A61K 33/26
(52) U.S. Cl. ....................... 424/647; 424/9.3; 424/9.323; 424/422; 424/423; 424/426; 424/428; 424/430; 424/434; 424/437; 514/502; 600/12; 607/103
(58) Field of Search ................................. 424/422–423, 424/426, 428, 430, 434–437, 489–491, 493–502, 647, 648, 1.29, 1.33, 1.53, 9.32–9.323; 514/502; 600/12; 607/103, 105

(56) References Cited

U.S. PATENT DOCUMENTS

| | | | | |
|---|---|---|---|---|
| 5,460,831 A | * | 10/1995 | Kossovsky et al. | 424/493 |
| 5,462,751 A | * | 10/1995 | Kossovsky et al. | 424/494 |
| 5,547,748 A | * | 8/1996 | Ruoff et al. | 428/323 |
| 5,616,311 A | * | 4/1997 | Yen | 424/1.33 |
| 5,922,537 A | * | 7/1999 | Ewart et al. | 435/6 |
| 6,045,821 A | * | 4/2000 | Garrity et al. | 424/450 |
| 6,103,379 A1 | * | 8/2002 | Margel et al. | 428/403 |

FOREIGN PATENT DOCUMENTS

| | | | |
|---|---|---|---|
| EP | 0667148 | * | 5/1994 |
| WO | 90/01295 | * | 2/1990 |

OTHER PUBLICATIONS

Hermentin Et Al Bioconjugate Chemistry Nov./Dec. #6 pp 411–418, (1990).*

* cited by examiner

*Primary Examiner*—Neil S. Levy
(74) *Attorney, Agent, or Firm*—Heller Ehrman White & McAuliffe LLP

(57) ABSTRACT

The invention relates to nanoscale particles suited especially for use in tumor therapy by hyperthermia. Said particles comprise a (preferably superparamagnetic) iron oxide-containing core and at least two shells surrounding said core. The (innermost) shell adjoining the core is an envelope which comprises groups capable of forming cationic groups and is broken down by human or animal tissue at such a slow rate as to allow for association of the core surrounded by said envelope with the surface of cells and/or for absorption of said core into the inside of cells. The outer shell(s) consist(s) of species having neutral and/or anionic groups which allow the nanoscale particles to appear to the outside as having a neutral or negative charge and which are broken down by human or animal tissue more rapidly than the innermost shell—and in so doing uncover the shells underneath—but still sufficiently slowly so as to ensure that the nanoscale particles are adequately distributed in a tissue infiltrated with same particles in a particular point.

18 Claims, No Drawings

NANOSCALE PARTICLES HAVING AN IRON OXIDE-CONTAINING CORE ENVELOPED BY AT LEAST TWO SHELLS

This application is a 371 of PCT/EP98/03761, filed Jun. 19, 1998.

The present invention relates to nanoscale particles having an iron oxide containing, ferri-, ferro- or (preferably) superparamagnetic core and at least two shells surrounding said core. Said particles may be used for medical purposes, particularly for tumor therapy by hyperthermia.

It is generally believed that in comparison to their benign counterparts, transformed cells (cancer cells) of most tumors have a higher phagocytosis activity. Reasons therefor are considered to be the invasive activity into adjacent tissues and the exocytosis of lytic enzymes associated therewith as well as a higher metabolic activity of said transformed cells. In striving for a more rapid cellular proliferation the cancer cells dedifferentiate and thereby lose part of their specifity towards normal signal transduction pathways and, generally towards transmembrane processes. Most recently such changes have been recognized by, e.g., the loss/mutation of the important cell adhesion proteins and glycoproteins of the cell surface which meanwhile are considered to represent one of the prerequisites for the uncontrolled growth of malignant cells. Thus it is known that like macrophages, cancer cells incorporate fragments of normal cells or of other cell debris and can endogenously convert them into utilizable nutrients inside lysosomes. The signal recognition by which the endocytosis process is initiated in tumor cells is still not clear on principle. However, from in vivo studies on intralesionally applied particle suspensions it can be inferred that the distribution within the tissue and the incorporation into tumor cells is mainly dependent on the size and the charge of the particles. In orientation studies the present inventors have observed that with neutrally to negatively charged particles the distribution within the tumor tissue (e.g. of the carcinoma of the mamma) into the interstitial space of the tissue (microcapillaries, septa, lobuli) is very high. If the distribution of such particles is promoted by heat the process of uniform distribution even is significantly enhanced. It is assumed that neutral to negatively charged particles interact only weakly with the extracellular receptor molecules and the glycokalyx. The explanation therefor are the much more frequently negatively charged ion channels and integral proteins on the surfaces of the cells. Almost always positively charged ions that serve either the signal transduction (e.g. in the case of $Ca^{2+}$) or the maintenance of the osmotic equilibrium (e.g. $Na^+$, $K^+$) are imported. The rather more unspecific incorporation takes place via positively charged groups of extracellular particles since in that case the cell can import utilizable biomblecules in most cases. Furthermore biogenous sugars are also recognized and imported, said importation being less specific with tumor cells due to dedifferentiated receptor molecules. Owing to higher metabolic activity and the frequently existing deficient oxygen supply of the tumor tissues, the tumor cell must furthermore conduct an anaerobic glycolysis to a much higher extent than normal cells, which in part also results in an excessive acidification of the tumor environment due to accumulation of lactate. A further result thereof is, however, also that due to the much lower energy yield of the anaerobic metabolic pathways the tumor cells consume much more substrate of high energy content which substrate therefore has to be imported into the cells in high amounts. Since endocytosis as such also is an energy consumptive process, the tumor cell is under time pressure: although by higher importation rates more substrate is imported, also much low-grade material is taken in that affords hardly any energy yield later. Additionally, the continuous division and synthesis processes consume so much energy that in this case the usually strictly controlled intake of materials from the surrounding environment would not be sufficient and a large part of the cells would die. Therefore it makes sense that the tumor cell has a survival edge with a high unspecific intracellular intake since it can certainly gain more energy more rapidly from the digestion of "raw" elements than in the case of the highly selective intake of fewer, more specific elements.

Through observations in cell cultures and in experimental tumors the present inventors have found that the intracellular incorporation rate of (highly) positively charged particles into tumor cells is up to 1000 times higher than that of comparable particles with neutral or negative surface charge. This is attributed to the high affinity of the positive charges of the particles towards the many negatively charged integral proteins and receptors on the cell surface. When observing a shorter period of time, e.g., 6 to 48 hours the tumor cells which are more active with respect to metabolism and division take in much higher amounts of such particles than normal cells, even with the affinity of the particles towards the surfaces of the normal cells being the same. If additionally the lower intake specifity of the tumor cells is taken into account there is a substantial overall difference in cellular intake which in theory should be exploitable for therapeutic purposes. For said purpose no systemic enrichment is necessary, but merely a skillful exploitation of surface charges for the adhesion of the particles to the cell surfaces of the tumor cells.

Particles having the highest achievable external positive charge become electrostatically bound to the cells within a few seconds and in the case of tumor cells they are also internalized within only 2 to 6 hours in such amounts that already by means of the intracellular proportion of the (nano-) particles alone compact cell pellets can be heated (to 45–47° C.) and deactivated in vitro by an external alternating magnetic field. However, in vivo a very poor distribution of such (highly) positively charged particles within the tissue is found. In comparison thereto, neutral or negatively charged particles show a better distribution within the tissue but become less well imported into the cells and are predominantly transported away by the RES instead. Thus, for example, studies with dextran-coated magnetite particles have shown that the dextran was degraded endogenously and thereby an optimum energy intake inside the tumor cells was prevented. The present inventors have furthermore found that even though magnetite particles provided with a coating having positive charges (e.g. based on aminosilane) were not degraded endogenously they showed a poor distribution within the tissue. It would therefore be desirable to have available particles which combine the properties of the two (magnetite) particles just described, i.e., on the one hand show a very good distribution within the tumor tissue and on the other hand are also incorporated well by the tumor cells.

According to the present invention it has now been found that such particles can be obtained by providing a (preferably superparamagnetic) iron oxide-containing core with at least two shells (coats), the shell adjacent to the core having many positively charged functional groups which permits an easy incorporation of the thus encased iron oxide-containing cores into the inside of the tumor cells, said inner shell additionally being degraded by the (tumor) tissue at such a low rate that the cores encased by said shell have sufficient time to adhere to the cell surface (e.g. through electrostatic interactions between said positively charged groups and negatively charged groups on the cell surface) and to subsequently be incorporated into the inside of the cell. In contrast thereto, the outer shell(s) is (are) constituted by species which shield (mask) or compensate, respectively, or even overcompensate the underlying positively charged groups of the inner shell (e.g. by negatively charged functional groups) so that, from without, the nanoscale particle having said outer shell(s) appears to have an overall neutral or negative charge. Furthermore the outer shell(s) is (are) degraded by the body tissue at a (substantially) higher rate than the innermost shell, said rate being however still low enough to give the particles sufficient time to distribute themselves within the tissue if they are injected punctually into the tissue (e.g. in the form of a magnetic fluid). In the course of the degradation of said outer shell(s) the shell adjacent to the core is exposed gradually. As a result thereof, due the outer shell(s) (and their electroneutrality or negative charge as seen from the exterior) the coated cores initially become well distributed within the tissue and upon their distribution they also will be readily imported into the inside of the tumor cells (and first bound to the surfaces thereof, respectively), due to the innermost shell that has been exposed by the biological degradation of the outer shell(s).

Thus, the present invention relates to nanoscale particles having an iron oxide-containing core (which is ferro-, ferror, preferably, superparamagnetic) and at least two shells surrounding said core, the (innermost) shell adjacent to the core being a coat that features groups capable of forming cationic groups and that is degraded by the human or animal body tissue at such a low rate that an association of the core surrounded by said coat with the surfaces of cells and the incorporation of said core into the inside of cells, respectively is possible, and the outer shell(s) being constituted by species having neutral and/or anionic groups which, from without, make the nanoscale particles appear neutral or negatively charged and which is (are) degraded by the human or animal body tissue to expose the underlying shell(s) at a rate which is higher than that for the innermost shell but still low enough to ensure a sufficient distribution of said nanoscale particles within a body tissue which has been punctually infiltrated therewith.

Preferably the substance for the core consists of pure iron oxide, particularly magnetite or maghemite ($\gamma$-$Fe_2O_3$). Examples of other substances for the core that may be employed according to the present invention are other pure iron oxides but also mixed oxides containing iron such as, e.g., those of the general formula $Me(II)Fe_2O_4$ wherein Me(II) is preferably Zn, Cu, Co, Ni or Mn (in the case of Me(II)=Fe the result is magnetite). Furthermore metals different from the above metals may also be present in the cores, for example alkaline earth metals such as Ca and Mg. Generally, the concentration of metal atoms different from iron atoms in the substance for the core is preferably not higher than 70, and particularly not higher than 35 metal atom-%. It is preferred, however that said iron oxide particles be pure iron oxide particles and particularly those which contain both Fe(III) and Fe(II), the ratio Fe(II)/Fe(III) ranging preferably from 1/1 to 1/3.

The term "nanoscale particles" as used in the present specification and in the claims is to denote particles having an average particle size (or an average particle diameter, respectively) of not more than 100 nm, preferably not more than 50 nm and particularly not more than 30 nm. According to the present invention said nanoscale particles preferably have an average particle size ranging from 1 to 40 nm, more preferred from 3 to 30 nm, a particle size of not more than 30 nm usually being a prerequisite for superparamagnetism.

It is particularly preferred for the core of the nanoscale particles according to the present invention to comprise (superparamagnetic) magnetite, maghemite or stoichiometric intermediate forms thereof.

The nanoscale particles according to the present invention usually have only two shells. However, it is also possible to provide more than one outer shell, e.g., two shells constituted by different species.

The exposed innermost shell (in closest proximity to the core) is a coat that is degraded at a relatively low rate by the human or animal body tissue (particularly tumor tissue) and has cationic groups or groups capable of forming cationic groups, respectively. Usually said groups consist of (positively charged) amino groups although according to the invention other positively charged or chargeable, respectively groups may be employed as well.

The cores of the nanoscale particles according to the present invention may be provided with the innermost shell in any manner and in a manner well known to the person skilled in the art. It must, however, be ensured that the innermost shell is degraded inside the (tumor) tissue at a rate which is sufficiently low to allow adhesion of the particles onto the cell surface and an importation of the particles into the cells (preferably tumor cells) and that said innermost shell has some—preferably as many as possible—cationic groups. Normally the innermost shell has on the average at least 50, preferably at least 100 and particularly at least 500 cationic groups (e.g., positively charged amino groups). According to a preferred embodiment of the present invention the coat is provided by using monomeric aminosilanes such as, e.g., 3-aminopropyltriethoxysilane, 2-aminoethyl-3-aminopropyltrimethoxysilane, trimethoxysilylpropyldiethylenetriamine and N-(6-aminohexyl)-3-aminopropyltrimethoxysilane. Preferably said silanes are applied onto said cores in known manner and are than subjected to polycondensation in order to achieve high stability. A method suitable for said purpose is described in, e.g., DE-A19614136. The corresponding disclosure is explicitly referred to herein. A further process suitable for the provision, around an iron oxide-containing core, of an innermost shell having cationic groups can be taken from, e.g., DE-A-19515820. Naturally other processes may be employed for said purpose as well.

According to the present invention one or more (preferably one) outer shells are provided on the described innermost shell. In the following discussion it is assumed that only one single outer shell is present. If more than one outer shell is desired, the additional shells are provided in analogous manner.

As already explained, the outer shell serves to achieve a good distribution within the tumor tissue of the iron oxide-containing cores having said inner shell, said outer shell being required to be biologically degradable (i.e., by the tissue) after having served its purpose to expose the underlying innermost shell, which permits a smooth incorporation into the inside of the cells and an association with the surfaces of the cells, respectively. The outer shell is constituted by species having no positively charged functional groups, but on the contrary having preferably negatively charged functional groups so that, from without, said nanoscale particles appear to have an overall neutral charge (either by virtue of a shielding (masking) of the positive charges inside thereof and/or by neutralization thereof by negative charges as may, for example, be provided by carboxylic groups) or even a negative charge (for example due to an excess of negatively charged groups). According to the present invention for said purpose there may be employed, for example, readily (rapidly) biologically degradable polymers suitable for coupling to the underlying shell (particularly innermost shell), e.g., (co)polymers based on α-hydroxycarboxylic acids (such as, e.g., polylactic acid, polyglycolic acid and copolymers of said acids), polyols (such as, e.g., polyethylene glycol) or polyacids (e.g. sebacic acid). The use of optionally modified, naturally occurring substances, particularly biopolymers, is particularly preferred for said purpose. Among the biopolymers the carbohydrates (sugars) and particularly the dextrans may, for example, be cited. In order to generate negatively charged groups in said neutral molecules one may employ, for example, weak oxidants that convert part of the hydroxyl or aldehyde functionalities into (negatively charged) carboxylic groups.

It must be emphasized, however, that in the synthesis of the outer coat one is not limited to carbohydrates or the other species recited above but that on the contrary any other naturally occurring or synthetic substances may be employed as well as long as they satisfy the requirements as to biological degradability (e.g. enzymatically) and charge or masking of charge, respectively.

The outer layer may be coupled to the inner layer (or an underlying layer, respectively) in a manner known to the person skilled in the art. The coupling may, for example, be of the electrostatic, covalent or coordination type. In the case of covalent interactions there may, for example, be employed the conventional bond-forming reactions of organic chemistry, such as, e.g., ester formation, amide formation and imine formation. It is, for example, possible to react a part of or all of the amino groups of the innermost shell with carboxylic groups or aldehyde groups of corresponding species employed for the synthesis of the outer shell(s), whereby said amino groups are consumed (masked) with formation of (poly-)amides or imines. The biological degradation of the outer shell(s) may then be effected by (e.g., enzymatic) cleavage of said bonds, whereby at the same time said amino groups are regenerated.

Although the essential elements of the nanoscale particles according to the present invention are (i) the iron oxide-containing core, (ii) the inner shell which in its exposed state is positively charged and which is degradable at a lower rate, and (iii) the outer shell which is biologically degradable at a higher rate and which, from without, makes the nanoscale particles appear to have an overall neutral or negative charge, the particles according to the invention still may comprise other, additional components. In this context there may particularly be cited substances which by means of the particles of the present invention are to be imported into the inside of cells (preferably tumor cells) to enhance the effect of the cores excited by an alternating magnetic field therein or to fulfill a function independent thereof. Such substances are coupled to the inner shell preferably via covalent bonds or electrostatic interactions (preferably prior to the synthesis of the outer shell(s)). This can be effected according to the same mechanisms as in the case of attaching the outer shell to the inner shell. Thus, for example in the case of using aminosilanes as the compounds constituting the inner shell, part of the amino groups present could be employed for attaching such compounds. However, in that case there still must remain a sufficient number of amino groups (after the degradation of the outer shell) to ensure the smooth importation of the iron oxide-containing cores into the inside of the cells. Not more than 10% of the amino groups present should in general be consumed for the importation of other substances into the inside of the cells. However, alternatively or cumulatively it is also possible to employ silanes different from aminosilanes and having different functional groups for the synthesis of the inner shell, to subsequently utilize said different functional groups for the attachment of other substances and/or the outer shell to the inner shell. Examples of other functional groups are, e.g., unsaturated bonds or epoxy groups as they are provided by, for example, silanes having (meth)acrylic groups or epoxy groups.

According to the present invention it is particularly preferred to link to the inner shell substances which become completely effective only at slightly elevated temperatures as generated by the excitation of the iron oxide-containing cores of the particles according to the invention by an alternating magnetic field, such as, e.g., thermosensitive chemotherapeutic agents (cytostatic agents, thermosensitizers such as doxorubicin, proteins, etc.). If for example a thermosensitizer is coupled to the innermost shell (e.g. via amino groups) the corresponding thermosensitizer molecules become reactive only after the degradation of the outer coat (e.g. of dextran) upon generation of heat (by the alternating magnetic field).

For achieving optimum results, e.g. in tumor therapy, the excitation frequency of the alternating magnetic field applicator must be tuned to the size of the nanoscale particles according to the present invention in order to achieve a maximum energy yield. Due to the good distribution of the particle suspension within the tumor tissue, spaces of only a few micrometers in length can be bridged in a so-called "bystander" effect known from gene therapy, on the one hand by the generation of heat and on the other hand through the effect of the thermosensitizer, especially if excited several times by the alternating field, with the result that eventually the entire tumor tissue becomes destroyed.

Particles leaving the tumor tissue are transported by capillaries and the lymphatic system into the blood stream, and from there into liver and spleen. In said organs the biogenous degradation of the particles down to the cores (usually iron oxide and iron ions, respectively) then takes place, which cores on the one hand become excreted and on the other hand also become resorbed and introduced into the body's iron pool. Thus, if there is a time interval of at least 0.5 to 2 hours between the intralesional application of magnetic fluid and the excitation by the alternating field the surrounding environment of the tumor itself has "purged" itself of the magnetic particles so that during excitation by the alternating field indeed only the lesion, but not the surrounding neighborhood will be heated.

In contrast to high molecular weight substances, nanoparticles do not leave the tissue into which they have been applied, but get caught within the interstices of the tissue. They will get transported away only via vessels that have been perforated in the course of the application. High molecular weight substances, on the other hand, leave the tissue already due to diffusion and tumor pressure or become deactivated by biodegradation. Said processes cannot take place with the nanoscale particles of the present invention since on the one hand they are already small enough to be able to penetrate interstices of the tissue (which is not possible with particles in the $\mu$m range, for example, liposomes) and on the other hand are larger than molecules and, therefore cannot leave the tissue through diffusion and capillary pressure. Moreover, in the absence of an alternating magnetic field, the nanoscale particles lack osmotic activity and hardly influence the tumor growth, which is absolutely necessary for an optimum distribution of the particles within the tumor tissue.

If an early loading of the primary tumor is effected the particles will be incorporated to a high extent by the tumor cells and will later also be transferred to the daughter cells at a probability of 50% via the parental cytoplasm. Thus, if also the more remote surroundings of the tumor and known sites of metastatic spread, respectively are subjected to an alternating magnetic field individual tumor cells far remote from the primary tumor will be affected by the treatment as well. Particularly the therapy of affected lymphatic nodes can thus be conducted more selectively than in the case of chemotherapy. Additional actions by gradients of a static magnetic field at sites of risk of a subsequent application of an alternating field may even increase the number of hits of loaded tumor cells.

As already mentioned above, thermosensitizers and/or cytostatic agents are preferably linked to the nanoscale particles according to the present invention (specifically the inner shell thereof). Only the magnetic coupling of the magnetic particles with the alternating magnetic field and the development of heat resulting therefrom brings about an activation or also a release of substances having cytotoxic action that have (preferably) been linked to the particles according to the present invention.

Due to the two-stage interlesional application a selective accumulation is not necessary. Instead the exact localization of the lesion determined in the course of routine examination and the subsequently conducted infiltration, in stereotactic manner or by means of navigation systems (robotics), of the magnetic fluid into a target region of any small (or bigger) size are sufficient.

The combination with a gradient of a static magnetic field permits a regioselective chemoembolization since not only the cyctostatic agent preferably present on the particles of the invention.is activated by heat but also a reversible aggregation of the particles and, thus a selective embolization may be caused by the static field.

In addition to tumor therapy, further applications of the nanoscale particles according to the present invention (optionally without the outer shell(s)) are the heat-induced lysis of clotted microcapillaries (thrombi) of any localization in areas which are not accessible by surgery and the successive dissolution of thrombi in coronary blood vessels. For example thrombolytic enzymes which show an up to tenfold increase in activity under the action of heat or even become reactive only on heating, respectively may for said purpose be coupled to the inner shell of the particles according to the invention. Following intraarterial puncture of the vessel in the immediate vicinity of the clogging the particles will automatically be transported to the "point of congestion" (e.g., under MRT control). A fiberoptical temperature probe having a diameter of, e.g., 0.5 mm is introduced angiographically and the temperature is measured in the vicinity of the point of congestion while, again by external application of an alternating magnetic field, a microregional heating and activation of said proteolytic enzymes is caused. In the case of precise application of the magnetic fluid and of MRT control a determination of the temperature can even be dispensed with on principle since the energy absorption to be expected can already be estimated with relatively high accuracy on the basis of the amount of magnetic fluid applied and the known field strength and frequency. The field is reapplied in intervals of about 6 to 8 hours. In the intervals of no excitation the body has the opportunity to partly transport away cell debris until eventually, supported by the body itself, the clogging is removed. Due to the small size of the particles of the invention the migration of said particles through the ventricles of the heart and the blood vessels is uncritical. Eventually the particles again reach liver and spleen via RES.

Apart from classical hyperthermia at temperatures of up to 46/47° C. also a thermoablation can be conducted with the nanoscale particles of the present invention. According to the state of the art mainly interstitial laser systems that are in part also used in surgery are employed for thermoablative purposes. A big disadvantage of said method is the high invasivity of the microcatheter-guided fiberoptical laser provision and the hard to control expansion of the target volume. The nanoparticles according to the present invention can be used for such purposes in a less traumatic way: following MRT-aided accumulation of the particle suspension in the target region, at higher amplitudes of the alternating field also temperatures above 50° C. can homogeneously be generated. Temperature control may, for example, also be effected through an extremely thin fiberoptical probe having a diameter of less than 0.5 mm. The energy absorption as such is non-invasive.

What is claimed is:

1. A method of hyperthermic treatment of a region of the body selected from the group consisting of hyperthermic tumor therapy, heat-induced lysis of a thrombus, and thermoablation of a target region, comprising:

(a) accumulating in the region of the body a magnetic fluid comprising nanoscale particles suspended in a fluid medium, each particle having an iron oxide-containing core and at least two shells surrounding said core,
      (1) the innermost shell adjacent to the core being a shell that:
         (a) is formed from polycondensable silanes comprising at least one aminosilane and comprises groups that are positively charged or positively chargeable, and
         (b) is degraded by human or animal body tissue at such a low rate that adhesion of the core surrounded by the innermost shell with the surface of a cell through said positively charged or positively chargeable groups of the innermost shell and incorporation of the core into the interior of the cell are possible, and
      (2) the outer shell or shells comprising at least one species that:
         (a) is a biologically degradable polymer selected from (co)polymers based on α-hydroxycarboxylic acids, polyols, polyacids, and carbohydrates optionally modified by carboxylic groups and comprises neutral and/or negatively charged groups so that the nanoscale particle has an overall neutral or negative charge from the outside of the particle, and
         (b) is degraded by human or animal body tissue to expose the underlying shell or shells at a rate which is higher than that for the innermost shell but is still low enough to ensure a sufficient distribution of a plurality of the nanoscale particles within a body tissue which has been infiltrated therewith; and
   (b) applying an alternating magnetic field to generate heat in the region by excitation of the iron oxide-containing cores of the particles, thereby causing the hyperthermic treatment.

2. The method of claim 1 that is a method of tumor therapy by hyperthermia, comprising accumulating in the tumor the magnetic fluid, and applying an alternating magnetic field to generate heat by excitation of the iron oxide-containing cores of the particles to cause hyperthermia in the tumor.

3. The method of claim 1 that is a method of heat-induced lysis of a thrombus, comprising accumulating in the thrombus the magnetic fluid, and applying an alternating magnetic field to generate heat by excitation of the iron oxide-containing cores of the particles to cause heat-induced lysis of the thrombus.

4. The method of claim 1 that is a method of thermoablation of a target region, comprising accumulating in the target region the magnetic fluid, and applying an alternating magnetic field to generate heat by excitation of the iron oxide-containing cores of the particles to cause thermoablation of the target region.

5. The method of claim 1 where the iron oxide-containing core comprises magnetite, maghemite, or stoichiometric intermediate forms thereof.

6. The method of claim 1 where the iron-oxide-containing core has an average particle size of 1 to 40 nm.

7. The method of claim 6 where the iron oxide-containing core has an average particle size of 3 to 30 nm.

8. The method of claim 1 where the iron oxide-containing core is superparamagnetic.

9. The method of claim 1 where the iron oxide-containing core is surrounded by only two shells.

10. The method of claim 1 where the innermost shell is derived from aminosilanes.

11. The method of claim 1 where the at least one species comprising the outer shell or shells is selected from carbohydrates optionally modified by carboxylic groups.

12. The method of claim 11 where the at least one species comprising the outer shell or shells is selected from dextrans optionally modified by carboxylic groups.

13. The method of claim 12 where the at least one species comprising the outer shell or shells is selected from dextrans modified by carboxylic groups.

14. The method of claim 1 where at least one pharmacologically active species is linked to the innermost shell.

15. The method of claim 14 where the at least one pharmacologically active species is selected from the group consisting of thermosensitizers and thermosensitive chemotherapeutic agents.

16. A method of tumor therapy by hyperthermia, comprising:

(a) accumulating in the tumor a magnetic fluid comprising nanoscale particles suspended in a fluid medium, each particle having a superparamagnetic iron oxide-containing core having an average particle size of 3 to 30 nm comprising magnetite, maghemite, or stoichiometric intermediate forms thereof and at least two shells surrounding said core, (1) the innermost shell adjacent to the core being a shell that:

(a) is formed from polycondensable aminosilanes and comprises groups that are positively charged or positively chargeable, and (b) is degraded by human or animal body tissue at such a low rate that adhesion of the core surrounded by the innermost shell with the surface of a cell through said positively charged or positively chargeable groups of the innermost shell and incorporation of the core into the interior of the cell are possible, and (2) the outer shell or shells being a shell or shells comprising at least one species that:

(a) is a biologically degradable polymer selected from dextrans optionally modified by carboxylic groups and comprises neutral and/or negatively charged groups so that the nanoscale particle has an overall neutral or negative charge from the outside of the particle, and (b) is degraded by human or animal body tissue to expose the underlying shell or shells at a rate which is higher than that for the innermost shell but is still low enough to ensure a sufficient distribution of a plurality of the nanoscale particles within a body tissue which has been infiltrated therewith; and (b) applying an alternating magnetic field to generate heat in the tumor by excitation of the iron oxide-contain cores of the particles, thereby causing hyperthermia of the tumor.

17. The method of claim 16 where at least one pharmacologically active species is linked to the innermost shell.

18. The method of claim 17 where the at least one pharmacologically active species is selected from the group consisting of thermosensitizers and thermosensitive chemotherapeutic agents.

* * * * *